(12) United States Patent
Konings

(10) Patent No.: US 10,278,598 B2
(45) Date of Patent: May 7, 2019

(54) METHOD FOR DETERMINING THE STROKE VOLUME OF A HEART, METHOD FOR DETERMINING THE ELECTRODE POSITIONS THEREFOR, AND SHEET SHAPED DEVICE THEREFOR

(75) Inventor: Maurits Karel Konings, Utrecht (NL)

(73) Assignee: Hemologic B.V., Amersfoort (NL)

( * ) Notice: Subject to any disclaimer, the term of this patent is extended or adjusted under 35 U.S.C. 154(b) by 677 days.

(21) Appl. No.: 13/143,709

(22) PCT Filed: Jan. 11, 2010

(86) PCT No.: PCT/NL2010/050011
§ 371 (c)(1),
(2), (4) Date: Sep. 21, 2011

(87) PCT Pub. No.: WO2010/080033
PCT Pub. Date: Jul. 15, 2010

(65) Prior Publication Data
US 2012/0059593 A1    Mar. 8, 2012

(30) Foreign Application Priority Data

Jan. 9, 2009 (NL) ...................................... 1036401
Jan. 6, 2010 (NL) ...................................... 2004064

(51) Int. Cl.
*A61B 5/029* (2006.01)
*A61B 5/0408* (2006.01)
(Continued)

(52) U.S. Cl.
CPC .......... *A61B 5/029* (2013.01); *A61B 5/04085* (2013.01); *A61B 5/0535* (2013.01); *A61B 5/0295* (2013.01)

(58) Field of Classification Search
CPC ..... A61B 5/02154; A61B 5/021; A61B 5/441; A61B 5/0205; A61B 5/0215;
(Continued)

(56) References Cited

U.S. PATENT DOCUMENTS 4,763,660 A * 8/1988 Kroll et al. ................... 600/391
6,511,438 B2   1/2003 Bernstein et al.

FOREIGN PATENT DOCUMENTS

NL      1015038      10/2001
WO   2005089056       9/2005

OTHER PUBLICATIONS

"Electrical Impedance methods for the measurement of stroke volume in man: state of art" by Vedru et al., Acta et Comm. Univ. Tartuensis, V. 974, pp. 110-129, 1994.*
(Continued)

*Primary Examiner* — Patricia Mallari
*Assistant Examiner* — Jairo H Portillo
(74) *Attorney, Agent, or Firm* — Rudy J. Ng; Bret E. Field; Bozicevic, Field & Francis LLP

(57) ABSTRACT

Method for determining the stroke volume of a heart comprising: attaching electrodes to the front legs or arms or head, and the hind legs of the body; connecting an alternating current source to the left pair of front legs/arms or head, and hind legs; connecting an alternating current source to the right pair of front legs/arms or head, and hind legs; attaching a number of electrode pairs to the thoracic skin, such that the electrodes are in contact with the skin of the thorax at predetermined positions, wherein the electrode pairs are each connected to an independent input of a data acquisition/calculation device; determining the beginning the cardiac cycle and measuring with the number of electrode pairs on the thorax the voltage at the beginning of the cardiac cycle at the predetermined positions; measuring during the cardiac
(Continued)

cycle with the number of electrode pairs on the thorax the voltages at the predetermined positions and determining the voltage changes $V_{meas}(\tau)$ compared to the voltage at the beginning of the cardiac cycle; decomposing the vector of voltage changes $V_{meas}(\tau)$ into an atrial component $\alpha(\tau)$, and ventricular component $\psi(\tau)$, wherein both components are proportional to the vector of measured thorax voltages $V_{meas}(\tau)$ by a weight factor $W_A$ and $W_v$ respectively; converting the ventricular component $\psi(\tau)$ to a ventricular stroke volume, by multiplying the ventricular component with a constant, the constant being a predetermined volume change $V_{calib}$ divided by a ventricular component $\varphi_{calib}$ of a predetermined calibration measurement.

10 Claims, 3 Drawing Sheets

(51) Int. Cl.
*A61B 5/053* (2006.01)
*A61B 5/0295* (2006.01)

(58) Field of Classification Search
CPC . A61B 5/02152; A61B 5/02216; A61B 5/022; A61B 5/02208; A61B 5/02225; A61B 5/023; A61B 5/0235; A61B 5/02233
USPC .......................................................... 600/484
See application file for complete search history.

(56) References Cited

OTHER PUBLICATIONS

"The technique of impedance cardiography" by Woltjer et al., European Heart Journal, V. 18, pp. 1396-1403, 1997.*
"Changes in electrical resistivity of swine liver after occlusion and postmortem" by Haemmerich et al., Medical and Biological Engineering and Computing, vol. 40, pp. 29-33, 2002.*
Patterson et al. 'Ventricular Volume Curves Obtained from Thoracic Impedance Measurements' Proceedings of the 20th Annual International Conference of the IEEE Engineering in Medicine and Biology Society, 1998, pp. 444-446, vol. 20(1).
Vonk-Noordegraaf et al. 'Determination of Stroke Volume by Means of Electrical Impedance Tomography; Determination of Stroke Volume By EIT' Physiological Measurement, Institute of Physics Publishing, May 1, 2000, vol. 21(2), pp. 285-293.

\* cited by examiner

METHOD FOR DETERMINING THE STROKE VOLUME OF A HEART, METHOD FOR DETERMINING THE ELECTRODE POSITIONS THEREFOR, AND SHEET SHAPED DEVICE THEREFOR

DESCRIPTION OF THE INVENTION

The measurement of cardiac output (CO) is important in the hemodynamic management of peri-operative and critically ill patients. Pulmonary artery thermodilution CO monitoring using the pulmonary artery catheter is still the clinical gold standard of CO-monitoring, but has major disadvantages, because pulmonary artery catheterization is time-consuming, and associated with a considerable risk of morbidity and mortality.

An ideal method to measure CO must be non-invasive, continuous, precise, operator-independent and cost-effective. Thoracic impedance cardiography meets a number of these requirements, but conflicting results concerning validity and reliability have been reported, varying from satisfactory correlations to poor correlations in comparison to thermodilution CO measurements. Analysis of a number of impedance cardiography (ICG) algorithms has indicated that the partly unsatisfactory performance of ICG may be attributed to three fundamental issues:

(i) The cylinder-, cube-, or cone-based models used in ICG to calculate CO have been shown to be not reliable when compared to thermodilution CO measurements. These models are oversimplifications of the complex motions of many structures that occur inside the thorax during the cardiac cycle. Therefore, in the invention described in this document, no such oversimplified models are used.

(ii) There is a need for an increase in the number of measurement input streams (independent voltage measuring electrode pairs) to balance the many unknown variables inside the thorax. Therefore, in the invention described in this document, a number (more than one) of electrode pairs are attached to the thoracic skin, such that the electrodes are in contact with the skin of the thorax at predetermined positions, wherein the electrode pairs are each connected to an independent input of a data acquisition/calculation device. In one embodiment at least a number of electrode pairs share a common reference electrode. In another embodiment, electrode pairs do not share common electrodes.

(iii) And, most importantly, ICG aims at measuring the variation of the total heart volume as function of time during the cardiac cycle. Total heart variation however is not a good indicator of stroke volume, as is explained directly below. During ventricular systole, the volume of the atria is increasing. The amount of change of the total heart volume during a single cardiac cycle strongly depends on the difference in speed by which the ventricles are emptying, and the atria are filling. The ventricles can achieve the same stroke volume by ejecting at a slower rate during systole, spreading the ventricular contraction more evenly over the entire systolic time interval. This however will result in a smaller total heart volume variation during the ventricular systole.

Indeed, Carlsson et al have shown that the variation of total heart volume during the cardiac cycle differs considerably between patients. This difference in total heart volume variation is not directly related to differences in stroke volume, but can have many causes. Therefore, it is important to be able to assess the volume changes of the ventricles alone, i.e., independently from the volume changes in the atria.

In this invention, a new method is presented for non-invasive, continuous, operator-independent electric measurement of exclusively ventricular stroke volume.

Like in ICG, in our invention we apply a weak, patient-safe, AC current on the patient's body, resulting in a weak electric current density field inside the thorax.

In contrast to ICG however, we do not aim at reconstructing any impedance measure. Instead, we retrieve the volume changes (as function of time during the cardiac cycle) of exclusively the ventricles, on the basis of measured shifts in voltage patterns on the thoracic skin of the patient, using N (N>1) independent voltage measuring electrode pairs, thus producing N independent input streams of continuously measured voltages. In a preferred embodiment, the value of N is N=6. These measured data are subsequently compared to voltage shifts that we measured in vitro during artificial filling of exclusively the ventricles in a post-mortem set-up, as will be explained below.

In order to describe the relations between stroke volume and measured shifts in the thoracic voltage distribution, we adopt a fundamental approach using a mathematical perturbation series, in which no assumptions are being made about the exact shape of the heart. Furthermore, we recognize that heart motion is very complex, and defies easy modeling. Therefore, the method of the invention does not involve any specific geometrical or mathematical modeling of cardiac motion.

Instead, an extensive set of in-vitro measurements has been performed, using human post-mortem hearts and thoraces. The valves inside the post-mortem human hearts were sealed, and each compartment of the heart was connected to a silicon tube leading to a large syringe, thus enabling the separate filling (or emptying) of e.g. only the ventricles, or only the atria.

The effect of the filling action on the applied thoracic current density distribution was registered by electrodes on the skin. In this way, a distinct 2D voltage pattern on the thoracic skin was measured representing the specific filling action of the ventricle alone. In the following, we will refer to such a 2D voltage pattern as a "fingerprint". Besides such a ventricular fingerprint, we measured an atrial fingerprint as well, representing the filling of only the atria.

In a living heart, volume changes in the ventricles take place simultaneously with volume changes in the atria. Therefore, the voltages that have been measured in-vivo on the thoracic skin of a patient, must be decomposed (by an algorithm) into a contribution originating from the ventricular volume changes, and a contribution originating from the atrial volume changes.

Our new method comprises an algorithm, of which it is the primary task to perform this decomposition into atrial and ventricular contributions, using the in-vivo measured thoracic skin voltages from the patient as an input, together with the standardized in-vitro atrial and ventricular fingerprint data.

The ventricular volume change during the cardiac cycle is the most important parameter to be measured, since the definition of ventricular stroke volume is directly related to ventricular volume change. The atrial volume change is a parameter that may be contaminated with artefacts, such as e.g. effects from isovolumetric motion. This is however no problem as long as the contaminating effects are separated from the pure ventricular volume change, and hence contaminate only the "atrial" parameter in the output of the algorithm.

During application of the invention on a patient, each independent electrode pair p produces a measured potential $v_{meas}(p)$. This measured potential $v_{meas}(p)$ is a linear combination of a purely atrial effect $\varphi_{atrial}$, and a ventricular effect $\varphi_{ventricular}$. The effect due to the isovolumetric contraction $\varphi_{isovolumetrisch}$ is comprised into the $\varphi_{atrial}$ as a contamination of the $\varphi_{atrial}$.

The algorithm needs to retrieve the factor $\psi(\tau)$ from the set of N equations (p=1, 2, . . . , N):

$$v_{meas}(p,\tau)=\psi(\tau)\varphi_{ventricular}(p)+\alpha(\tau)\varphi_{atrial}(p)$$

for each moment $\tau$ during the cardiac cycle.

Furthermore it is not necessary to cover the whole thorax of a patient with measuring electrodes to use our methodology: a crucial subset of 6 electrode pairs is sufficient (but a lower number of electrodes could still yield reasonable results), thus making it possible to design a disposable, self-adhesive, compound "electrode sticker", which can be applied on the thorax easily, quickly, and without discomfort to the patient.

The choice of the positions of the electrodes is an essential part of the method of the invention. The method for finding these electrode positions is based on the discovery (by the inventor) during the in-vitro experiments of the fact that the shifts in the applied current density fields due to Ventricular filling (without atrial volume changes), as measured on the thoracic skin, show a marked and rather concentrated maximum that is located on the thoracic skin near the caudal side of the ventricles (about 2 cm above the underside of the heart). One of the electrodes should therefore be placed on, or near, this "ventricular maximum". Furthermore, it has been discovered that the shifts in the applied current density fields due to Atrial filling (without ventricular volume changes), show a more diffuse pattern on the thoracic skin, with exception of a clear extremum that is located about 8 cm to 15 cm from the "ventricular maximum" in the caudal direction. Another electrode should therefore be placed on, or near, this "atrial extremum".

DETAILED DESCRIPTION

Redundancy:

There were (many) redundant electrodes arranged, so that the algorithm (during the initialization phase, see below) can select per patient which electrode positions give the clearest signals (empirical search for the precise location of the ventricular maximum per patient).

Fine-Tuning of the Weight Factors:

The variation in thoracic anatomy between patients is considerable, and this would pose a threat to the reliability of the method of the invention, unless neutered in a fundamentally robust manner.

Below, we present a new and fundamentally robust method to neuter inter-patient anatomical variations. It is constituted by two distinct neutering components that are integrated into the method of the invention:

An algorithm to neuter the effects of variation in thoracic subcutaneous fat and muscle layers, invoking the principle of reciprocity, and a "search" algorithm, that adapts the reconstruction parameters, as well as the choice of measuring electrodes, on basis of "pilot" measurements during the initialization phase. This initialization phase may repeated whenever a change in the posture or position of the patient produces significant alterations in the relative position of the heart with respect to the thoracic bone structure.

Of these two algorithms, the search algorithm is the most complex and critical.

The fundamental ideas underlying the search algorithm are presented below.

The search algorithm is based on the combination of two fundamental concepts:

(i) The (empirical) fact that whenever the thoracic anatomy of a patient (or volunteer) deviates from the "ideal" standard anatomy used in the volume-time reconstruction algorithm (see paper 1A), this translates into extra indentations, or wobbles or "waves" in the reconstructed ventricular volume-time curves.

(ii) The first order or second order derivative (with respect to time) of the ventricular volume-time curve constitutes a measure of the kinetic energy of the blood displacement through the aortic valve. On basis of the distribution in time (and hence the Fourier components) of the second derivative of the ventricular volume-time curve, this kinetic energy can be divided into two components:

1) Translational kinetic energy, contributing to the stroke volume. This is characterized by a second derivative that changes sign only sparsely. In physics, this corresponds to a displacement of blood volume into primarily one single direction.

2) Oscillatory kinetic energy. This is characterized by a second derivative that changes sign frequently. This corresponds to an oscillatory motion of the blood volume.

An essential point used by the new search algorithm is the fact that—from the viewpoint of physics—high-amplitude high-frequency oscillations are improbable due to the high specific weight of blood.

Such "violent, heavy-weight" oscillations have therefore two specific characteristics at the same time: they are likely to be unphysical (i.e., produced by the volume-time reconstruction algorithm due to a mismatch between ideal and actual thoracic anatomy), and they contribute highly to the overall energy content in the volume time-curve.

Minimization of Oscillatory Kinetic Energy, Scale-Invariance and Fourier Transform:

Calculation of the first or second order time-derivative of the reconstructed volume-time curves is cumbersome in the time-domain, because of discretization and high-frequency scale artifacts.

In the Fourier domain however, the first or second order time-derivative of any volume time curve $v(t)$ (having Fourier transform $\Im[v(t)]=\zeta(\omega)$), simply equals:

$$\Im[(d^2/dt^2)v(t)]=-\omega^2\zeta(\omega) \quad (1)$$

Invoking the Parseval theorem, we create a scale-invariant measure $\vartheta$ that we wish to minimize during the search algorithm.

This scale-invariant measure $\vartheta$ represents the ratio of the power (in the Parseval sense) of the second order time-derivative of $v(t)$, divided by the power of the (in the Parseval sense) of the $v(t)$ curve itself:

$$\vartheta = \frac{\sum(\omega^2\zeta(\omega))^2}{\sum(\zeta(\omega))^2} \quad (2)$$

in which the summation runs over the frequencies $\omega$.

Within the Fourier domain, appropriate filtering (Gaussian) is applied to avoid contribution of high-frequency noise into equation (2). As is clear from equation (2), the ratio $\vartheta$ is invariant under amplitude scaling of the entire volume-time curve.

In order to produce a realistic and robust search algorithm that is capable of neutering the vast gamma of inter-patient thoracic anatomical variations, the thoracic sensitivity distributions ("fingerprints") of a number of volunteers have been studied.

The most critical region for accurate electrode positioning on the thorax is the direct environment of the "ventricular maximum".

Therefore, the ventricular maximum is taken as a central point for scaling operations (virtual stretching of the thoracic landscape) by the search algorithm.

Furthermore, the z-position of the ventricular maximum may vary considerably between patients (and volunteers), making an overall virtual translation of the electrodes over the thoracic landscape necessary.

In summary, there are two parameters describing the "search space" for the search algorithm in which the minimum value of the ratio $\vartheta$ has to be found:

The shift in position of the ventricular maximum in the z direction (in mm), and a scaling factor representing the scaling operation in the z-direction having this position as the origin.

The present invention relates to a system for measuring the pumping action of the heart, i.e., in addition to the ventricular stroke volume, the atrial and the ventricular filling curves as a function of time during the cardiac cycle, the system comprising:

three or more surface electrodes to be arranged on the thorax;

electronic means for measuring during a cardiac cycle the voltage changes relative to the voltage value at the beginning of a cardiac cycle;

wherein the measurements are decomposed into an atrial filling and a ventricular filling, taking into account an isovolumetric contraction phase at the beginning of the cardiac cycle.

According to the system of the present invention, changes in voltage during the cardiac cycle are determined relative to these changes in voltage at the beginning of the cardiac cycle such as can be derived from the ECG.

An obtained three-dimensional measurement vector is preferably decomposed mathematically into three so-called basic vectors, i.e. the vector (the effect) of only atrial filling, the vector (the effect) of only ventricular filling and the vector (the effect) relating to the movement of the heart in the thorax which can be determined during the isovolumetric contraction phase at the beginning of the cardiac cycle. The isovolumetric effect can however also be seen as contamination of the atrial effect vector, so that the isovolumetric effect vector is dispensed with as independent vector.

It will be apparent that, by measuring both atrial and ventricular filling as a function of time, for instance between 0 and 800 milliseconds (ms), much better information concerning the heart function is obtained according to the present invention.

Compensation for instance the thickness of the fat layer and the location of the heart is preferably made for each patient during the so-called initialization phase by using pairs of electrodes temporarily as excitation electrodes carrying current, while measurement is performed by the other electrode pairs.

The present invention also provides a sheet-shaped device provided with three or more electrodes at predetermined positions relative to each other, wherein the sheet-shaped device is attachable to the thorax.

The present invention also provides a method for measuring the stroke volume of the heart, wherein the system comprises the following steps of:

arranging three or more surface electrodes on the thorax;

measuring voltage changes during a cardiac cycle relative to the voltage value at the beginning of a cardiac cycle; and decomposing the measurement results into data relating to an atrial filling and data relating to a ventricular filling, wherein account is taken of an isovolumetric contraction phase at the beginning of the cardiac cycle.

Further advantages, features and details of the present invention will be elucidated on the basis of the following description of a preferred embodiment thereof, wherein reference is made to the accompanying drawings, in which.

Figure 1:
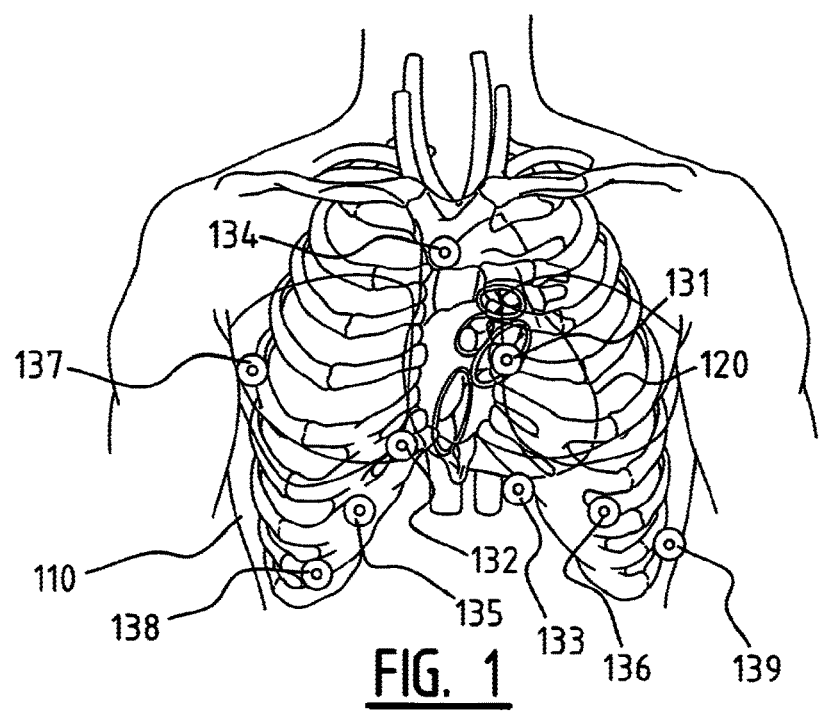
FIG. 1 shows a partially schematic front view of a thorax having arranged thereon a sheet-shaped device with electrodes for an embodiment of a system and method according to the present invention.
Figure 2:
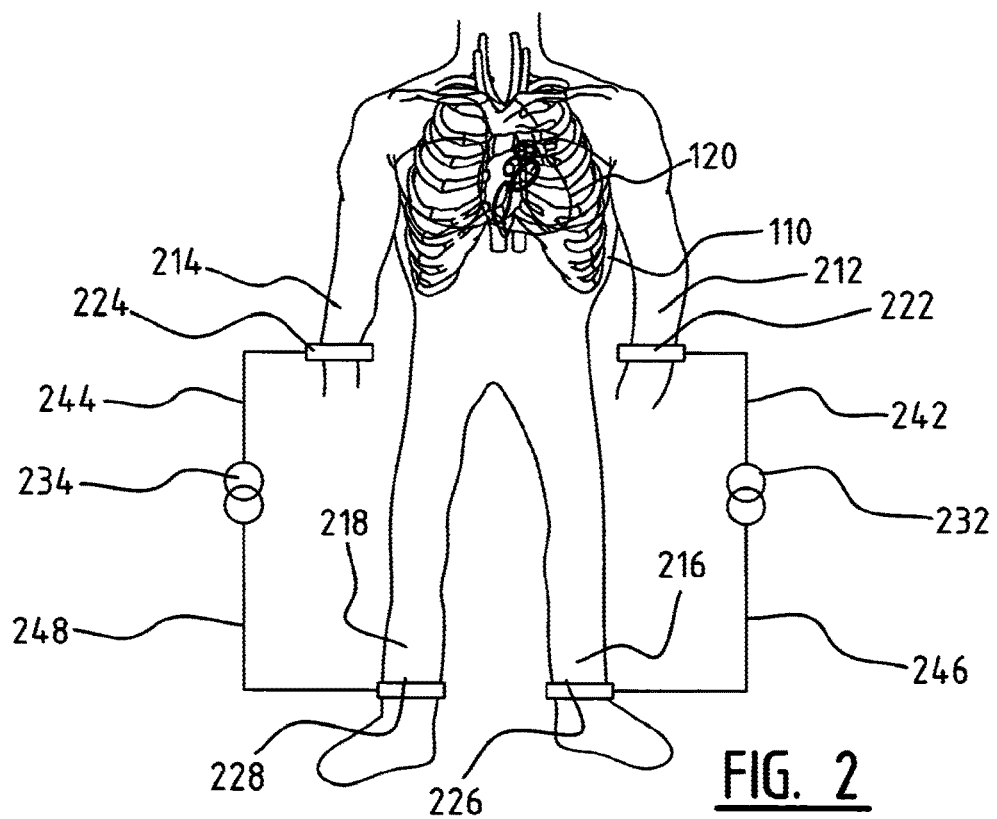
FIG. 2 shows a schematic front view of a human body with current sources connected for generating a potential field for the purpose of determining the heart stroke volume in accordance with a method according to the present invention.

For the purpose of determining the atrial filling and the ventricular filling a sticker or plaster (not shown) comprising at least six measuring electrodes is arranged on the thorax 110 (FIG. 1). In the shown embodiment the sticker is provided with nine measuring electrodes 131-139. Because the measuring electrodes are arranged at predetermined positions on the sticker, it is possible in simple manner to arrange the measuring electrodes at the correct position on the thorax 110. The sticker is provided for this purpose with at least one marker which must be aligned with a reference point to be found on the thorax 110, such as for instance the lower end of the sternum. The measuring electrodes are arranged at an advantageous position on the thorax 110 by correctly aligning the marker with the reference point and further orienting the sticker correctly, for instance on the basis of an orientation marker.

The measuring electrodes are ordered in groups of three electrodes which will be referred to as triplets. In the shown embodiment measuring electrodes 131, 132 and 133 together form the so-called C-triplet, or Center-triplet. Measuring electrodes 134, 135 and 136 together form the so-called H-triplet, or the Heart-triplet. Finally, measuring electrodes 137, 138 and 139 form the so-called L-triplet, or the Large-triplet. The measuring electrodes of the different triplets preferably lie at increasing distance from the point on the thorax which, stated simply, corresponds to the centre of the heart, as also shown in FIG. 1.

In the shown embodiment the upper (most cranially placed) electrode of each triplet is deemed the reference electrode. Two potential differences are thus determined for each triplet, i.e. between the respective two remaining electrodes in the triplet and the reference electrode in the triplet. In the shown embodiment in which three triplets are used, six different potential differences are thus shown. For the C-triplet the potential difference between respectively electrode 131 and 132 and between 131 and 133. For the H-triplet between respectively electrode 134 and 135 and between 134 and 136. And finally for the L-triplet between respectively electrode 137 and 138 and between 137 and 139.

In order to generate a potential field in the thorax conductive wristbands 222, 224 and ankle bands 226, 228 are arranged round respectively the wrists 212, 214 and ankles 216, 218. A current source 232, 234 is then connected to a wristband 222, 224 and an ankle band 226, 228. A first current source 232 ensures that an electrical alternating current with constant current amplitude flows via the left wrist 212, the left arm, through the thorax 110 and through the left leg to the left ankle 216. A second power source ensures that an alternating current with constant current amplitude flows via the right wrist 214, the right arm, through the thorax 110 via the right leg to the right ankle 218. The choice of amplitude of the current generated by current sources 232, 234 is sufficiently low to have no adverse consequences for the safety of the patient. A frequency of 64 kHz can for instance be chosen as frequency of the alternating current sources.

The potential field thus generated by the current sources can now be measured by means of electrodes 131-139 (FIG. 1). An initialization phase takes place in the first instance for this purpose.

During the initialization phase all electrodes 131-139 are measured in order to determine which triplet is positioned most optimally relative to the heart 120 for the specific patient on which measurements are being made. Reciprocity measurements are also performed an electrodes 131-139 during this phase. Owing to variations between patients, such as for instance variations in the thickness of the subcutaneous fat layer, the signals of the diverse electrodes 131-139 are each individually attenuated. In order to determine this attenuation a reciprocity measurement is performed on each electrode pair by exciting each electrode pair one by one using a current source. The other electrode pairs meanwhile measure the thus generated change in voltage. The attenuation factor $ATTENUATION_p$ of each electrode pair p is determined on the basis of the principle of reciprocity. This principle of reciprocity, a principle known from so-called 'lead fields', is invoked here to enable the measuring results, which are obtained during the initialization phase (when excitation takes place with the electrodes used as measuring electrodes in the normal measuring phase (i.e. not the initialization phase), to be interpreted as attenuation factors; wherein these attenuation factors can subsequently be applied during the normal (non-initialization) phase when excitation does not take place via the electrodes on the thorax but via electrodes attached to the extremities (arms or legs) of the body.

Finally, the effect of the isovolumetric movement of the heart 120 can be determined during the initialization phase; this isovolumetric effect can however also be seen as contamination of the atrial component, or be wholly disregarded. This is discussed elsewhere in this document.

Once the optimum triplet and the attenuation factor $ATTENUATION_p$ applicable for each electrode pair has been determined during the initialization phase, the actual measurement begins. The potential field generated by the current sources causes a potential $\Phi(x)$ at each point x on the skin of the thorax. A movement of a boundary surface in the thorax, for instance a displacement of a part of the heart wall due to contraction of heart 120, causes a potential change $\varphi(x)$ at each point x. If a contour graph is displayed on the thorax, wherein the contours connect all points x of equal potential change $\varphi(x)$, a contour patterns then results around the point on the thorax lying closest to the moved boundary surface. In this pattern the potential change $\varphi(x)$ decreases the further the point x is away from the moved boundary surface. Each boundary surface movement hereby has a characteristic potential change pattern. Using the electrode pairs p the potential changes $v_{meas}(p, \tau)$ can now be measured. The change is measured here relative to the beginning of the cardiac cycle, this moment being Indicated by the ECG R-peak.

The boundary surface movements of heart 120 which take place during a cardiac cycle can be summarized as solely a translation/rotation of heart 120, solely an atrial filling or emptying and solely a ventricular filling or empty. The measured $v_{meas}(p, \tau)$ is therefore a linear combination of an atrial potential change $\varphi_{atrial}$, a ventricular potential change $\varphi_{ventricular}$ and an isovolumetric potential change $\varphi_{isovolumetrisch}$:

$$v_{meas}(p,\tau)=\alpha(\tau)\varphi_{atrial}+\psi(\tau)\varphi_{ventricular}+\gamma(\tau)\varphi_{isovolumetrisch}$$

The $\gamma(\tau)$ can by definition here also be set to equal zero so that the isovolumetric effects are included as an artefact (contamination) in the atrial component; only $\alpha(\tau)$ and then $\psi(\tau)$ then remain as variables.

As stated above, the influence of the isovolumetric movements is determined during the initialization phase. The isovolumetric contraction of heart 120 takes place immediately following the ECG R-peak. During this phase the volume of the atria and the ventricles remains the same, and $\alpha(\tau)$ and $\psi(\tau)$ thus equal zero. During this phase $v_{meas}(p, \tau)$ therefore consists only of $\gamma(t) \varphi_{isovolumetrisch}$, and this latter is determined by measuring the potential change for each electrode pair p. The isovolumetric component is however preferably deemed as artefact of the atrial component.

The atrial and ventricular components $\varphi_{atrial}$ and $\varphi_{ventricular}$ are determined beforehand in an in-vitro setup. Using this information it is now possible to determine at any moment in the cardiac cycle the atrial degree of filling $\alpha(t)$ and the ventricular degree of filling $\psi(\tau)$ by decomposing the measured potential change vector $v_{meas}(\tau)$.

Figure 3:
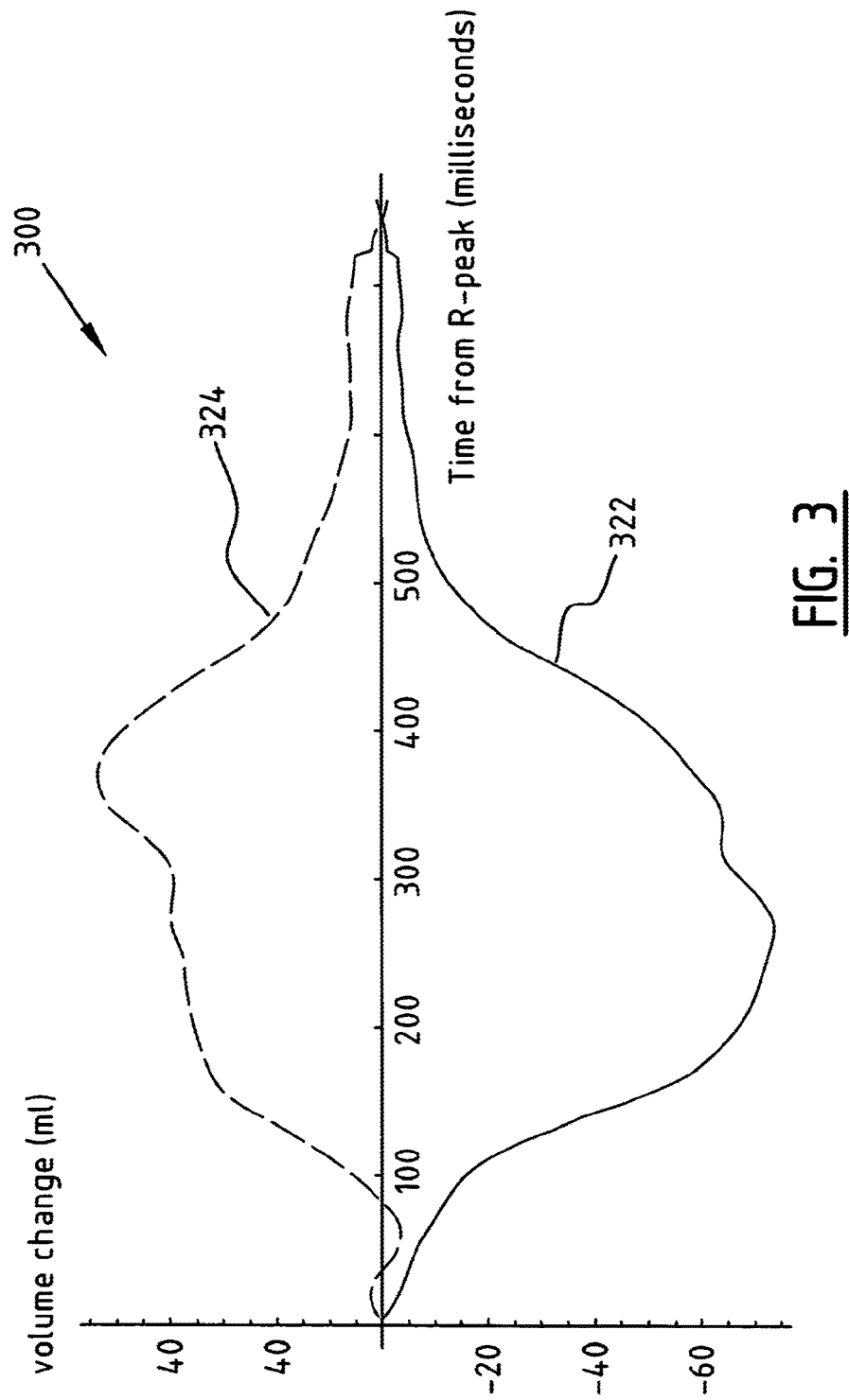
FIG. 3 shows measured changes in volume as a function of time during respectively the atrial and ventricular filling phases of the cardiac cycle.
Figure 4:
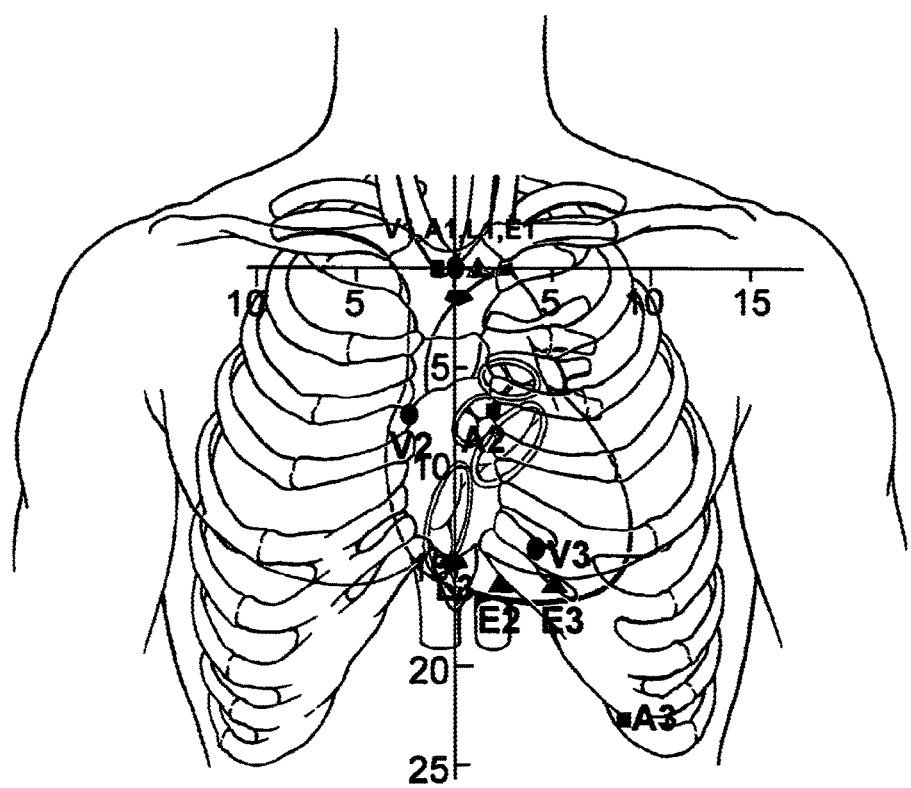
FIG. 4 shows a partially schematic front view of a thorax having arranged thereon a sheet-shaped device with electrodes for a preferred embodiment of a system and method according to the present invention.

A representation of the change in the atrial filling 324 generated according to a method of the invention is shown in the graph 300 of FIG. 3. The horizontal axis shows the time, wherein the zero point is determined by the R-peak of the electrocardiogram (ECG). The vertical axis shows the volume change of the atria and ventricles. The same graph 300, in addition to showing the change in the atrial filling 324, also shows the change in the ventricular filling 322.

It will be apparent to the skilled person that the above described embodiments according to the invention are only exemplary embodiments. Many modifications of the shown embodiments are possible within the invention. It is thus possible to combine all shown embodiments without departing from the present invention. The protection sought is defined by the appended claims.

The invention claimed is:

1. A method for decomposing a vector of measured thorax voltages during a cardiac cycle of a heart of a human or animal body, wherein the heart is comprised in a thorax of the body, and wherein the body comprises a plurality of appendages including a head, two front legs or two arms, and two hind legs or two legs, the method comprising:
   attaching one or more electrodes to the front legs or the arms or the head, and the hind legs or legs of the body;
   connecting an alternating current source to a first pair of appendages, wherein the first pair of appendages includes a left front leg or a left arm or the head, and a left leg or a left hind leg;

connecting an alternating current source to a second pair of appendages, wherein the second pair of appendages includes a right front leg or a right arm or the head, and a right leg or a right hind leg;

attaching a plurality of electrode pairs to a thoracic skin surface of the body, such that the electrodes are in contact with the thoracic skin surface of the body at a plurality of predetermined positions;

decomposing a vector of thorax voltages into an atrial component and a ventricular component;

determining a beginning of a cardiac cycle and measuring with the number of electrode pairs on the thoracic skin surface a voltage at the beginning of the cardiac cycle at the predetermined positions;

measuring during the cardiac cycle with the number of electrode pairs on the thoracic skin surface a plurality of voltages at the predetermined positions and determining a plurality of voltage changes vmeas($\tau$) compared to the voltage at the beginning of the cardiac cycle to determine a vector of thorax voltages;

analyzing the vector of thorax voltages to decompose the vector into an atrial component $\alpha(\tau)$ and a ventricular component $\psi(\tau)$ using an algorithm that includes a plurality of standardized in-vitro atrial and ventricular fingerprint data as well as an atrial weight factor wA and a ventricular weight factor wV; and multiplying the ventricular component with a constant, the constant being a predetermined volume change Vcalib divided by a ventricular component (pcalib of a predetermined calibration measurement, to obtain a measure of ventricular stroke volume.

2. The method according to claim 1, further comprising: determining a respiration cycle; and
ignoring a cardiac cycle that occurs when a lung volume change exceeds a threshold.

3. The method according to claim 1, comprising:
attaching in the proximity of at least part of the electrodes a further number of electrodes to the thoracic skin surface of the body, wherein the further number of electrodes are connected to a switching member, which switching member is adapted to select an optimal sub-set of electrodes for a particular patient under examination.

4. The method according to claim 1, further comprising:
directly or indirectly calculating a first or second order time-derivative of the multiplied ventricular component;
minimizing an oscillatory energy using the first order or second order time-derivative by varying the weight factors wV and wA for each electrode pair.

5. The method according to claim 1, wherein attaching a plurality of electrode pairs to a thoracic skin surface of the body comprises attaching a sheet shaped device to the thoracic skin surface of the body, wherein the sheet shaped device comprises:
a ventricular electrode (V3), located such that when the device is placed on a human or animal body having a heart and a thorax, the ventricular electrode (V3) is located near a caudal side of the heart;
an atrial electrode (A3), located at a distance between 80 and 150 mm from the ventricular electrode (V3); and
a reference electrode located near an incisura jugularis on the thorax.

6. The method according to claim 1, wherein attaching a plurality of electrode pairs to a thoracic skin surface of the body comprises attaching a sheet shaped device to the thoracic skin surface of the body, wherein the sheet shaped device comprises:
three or more electrodes and at least one marker to guide an operator during application of the sheet shaped device to a placement of the sheet shaped device on the thorax that results in:
a ventricular electrode (V3) positioned approximately 20 mm above a caudal edge of the heart;
an atrial electrode (A3) positioned at approximately 80 to 150 mm in a caudal direction with respect to the ventricular electrode (V3); and
a reference electrode positioned near an incisura jugularis on the thorax, or at any other position on the body of the patient that is sufficiently far away from the heart and any parts of the thorax that move during respiration.

7. The method according to claim 1, wherein attaching a plurality of electrode pairs to a thoracic skin surface of the body comprises attaching a sheet shaped device to the thoracic skin surface of the body, wherein the sheet shaped device comprises:
a first ventricular electrode (V1);
a second and/or a third ventricular electrode (V2, V3);
wherein, when the sheet shaped device is properly applied to the thorax,
the first ventricular electrode (V1) is located in the middle of an incisura jugularis on the thorax, or any other position on the thorax that is sufficiently far away from the heart and any parts of the thorax that move during respiration,
the third ventricular electrode (V3), if present, is located near a caudal edge of the heart, and
the second ventricular (V2) is located approximately 30 mm left of and 70 mm below the incisura jugularis on the thorax.

8. The method according to claim 1, wherein attaching a plurality of electrode pairs to a thoracic skin surface of the body comprises attaching a sheet shaped device to the thoracic skin surface of the body, wherein the sheet shaped device comprises:
a first atrial electrode (A1); and
a second and/or a third atrial electrode (A2, A3); wherein, when the sheet shaped device is properly applied to the thorax,
the first atrial electrode (A1) is located in the middle of an incisura jugularis on the thorax, or any other position on the thorax that is sufficiently far away from the heart and any parts of the thorax that move during respiration,
the third atrial electrode (A3), if present, is located approximately 50 mm right of and 210 mm below a cranial ending of a sternum on the thorax, and
the second atrial electrode (A2) is located approximately 15 mm right of and 70 mm below the cranial ending of the sternum on the thorax.

9. The method according to claim 1, wherein attaching a plurality of electrode pairs to a thoracic skin surface of the body comprises attaching a sheet shaped device to the thoracic skin surface of the body, wherein the sheet shaped device comprises:
a self-adhesive electrode sticker that comprises nine measuring electrodes and at least one marker which is configured to be aligned with a reference point to be found on a thorax, wherein the measuring electrodes are ordered in groups of three triplets, said groups comprising a center-triplet, a heart-triplet and a large triplet, wherein the most cranially-placed electrode of each triplet is configured to be placed as a reference electrode suitable for determining a potential difference between the respective two remaining electrodes in the triplet and the reference electrode in the triplet.

10. The method according to claim 1, wherein the measure of ventricular stroke volume changes as a function of time during the cardiac cycle.

\* \* \* \* \*